United States Patent [19]
Fleenor

[11] Patent Number: 5,741,280
[45] Date of Patent: Apr. 21, 1998

[54] KNOT TYING METHOD AND APPARATUS

[75] Inventor: Richard P. Fleenor, Englewood, Colo.

[73] Assignee: Coral Medical, Englewood, Colo.

[21] Appl. No.: 556,662

[22] Filed: Nov. 13, 1995

Related U.S. Application Data

[63] Continuation-in-part of Ser. No. 182,609, Jan. 18, 1994, abandoned.

[51] Int. Cl.⁶ .................................................. A61B 17/00
[52] U.S. Cl. .......................... 606/148; 606/139; 112/169
[58] Field of Search ........................... 606/148, 144, 606/145, 139, 151; 112/169, 80.03

[56] References Cited

U.S. PATENT DOCUMENTS

| | | | |
|---|---|---|---|
| 5,312,423 | 5/1994 | Rosenbluth et al. | 606/148 |
| 5,318,578 | 6/1994 | Hasson | 606/144 |
| 5,320,630 | 6/1994 | Ahmed | 606/139 |
| 5,454,821 | 10/1995 | Harm et al. | 606/148 |
| 5,527,323 | 6/1996 | Jervis et al. | 606/148 |

*Primary Examiner*—Jeffrey A. Schmidt
*Attorney, Agent, or Firm*—Davis, Graham & Stubbs LLP

[57] ABSTRACT

A method and apparatus for placing a knot such as a laparoscopy knot. Knot material containing a knot is wound around a ferrule surrounding a cylinder. A second ferrule surrounds the first ferrule so that the edge of the second ferrule abuts and attaches to the end windings of the knot material. Sliding the second ferrule pushes the windings of knot material including the knot off of the first ferrule and free of the cylinder. The cylinder, ferrules, and knot material containing the knot may be assembled as one disposable unit.

7 Claims, 3 Drawing Sheets

KNOT TYING METHOD AND APPARATUS

This is continuation-in-part of U.S. application Ser. No. 08/182,609 filed Jan. 18, 1994 now abandoned.

FIELD OF THE INVENTION

The present invention relates to the broad field of knot tying, and particularly knot tying in the context of medicine such as the tying of sutures. More specifically, the invention has special applicability to the placement and tying of sutures and other knots in the field of laparoscopic surgery.

BACKGROUND OF THE INVENTION

Knot tying and suturing as a method to approximate tissue is a critical element of surgery. Skill in knot tying is so basic to surgery that medical students learn knot tying early in their studies, and they routinely practice tying various kinds of knots with one or both hands.

In laparoscopic procedures, the tying of sutures and other knots is especially difficult and it is not uncommon for the tying of a single knot to require an hour or more. In laparoscopy, there is no tactile sense to the surgeon because of the surgeon's lack of direct contact with the tissue, since the surgeon's sense of feel is reduced by the imposition of the laparoscopic instruments. Further, the surgeon is unable to view directly the site of the surgery, but instead must rely upon a two-dimensional video screen which both magnifies the site and eliminates the opportunity for any depth perception.

Another difficulty is presented by the fact that laparoscopic surgery necessarily is conducted in a confined space, and the instruments are preferably positioned in this confined space in a particular orientation in relation to one another and in relation to the patient. For example, it is desirable that within this confined space, the instruments not be too close together or too far apart, that they be visible through the laparoscope, and that they enter the field of view of the laparoscope tangentially rather than coaxially so that they do not obstruct the view too much. It is also desirable that the instruments advance out of their sheaths toward the video screen and away from the laparoscope in order to avoid the surgeon having to operate under "mirror vision". Finally, procedures employing a single operating port encourage the surgeon to use the dominant hand to manipulate the instrument in the port while using the other hand merely to stabilize the laparoscopic sheath. However, knot tying typically requires both hands, and so an assistant or a device is then necessary to stabilize the sheath while both the surgeon's hands tie the knot.

Suturing and other knot tying are applicable to many different laparoscopic procedures. In laparoscopic cholecystectomy, the cystic duct or artery can be ligated using manual suturing or knot tying techniques rather than an automatic clip. In a laparoscopic appendectomy, the surgeon can use slip knots rather than using a disposable linear stapler. Although laparoscopic staplers have been developed, laparoscopic sutures and other knots will still be needed for many purposes such as closing defects in a staple line, placing purse-string sutures for end-to-end stapling, closing mesenteric defects, and ligating large blood vessels.

Knots used in laparoscopy may be tied either intracorporeally or extracorporeally. Internal knotting requires a high level of expertise by the surgeon, and normally requires at least two operating cannulae and associated graspers. For a square knot, a loop is made in a first end of the material using the first grasper; the second grasper is inserted through the loop and used to grasp the second end; the second end is pulled through the loop to produce a flat knot; another loop is made in the first end of the material using the first grasper; the second grasper is inserted through that loop and used to grasp the second end; and the second end is pulled through that loop to produce an opposing flat knot. The resulting square knot can then be tightened with the two graspers. The first throw may be a simple overhead knot or may be a surgeon's knot. Additional throws may be applied over the second throw to provide additional security. It is important that sequential throws are in opposite directions to avoid producing a "granny" knot.

Many other types of knots are possible depending on the characteristics of the material used, the dexterity of the surgeon, and the circumstances at the suture site. Many knots in laparoscopy are slip knots of some kind to allow the knot to be cinched against the sutured material. These include the Roeder knot, a cinch knot, and so-called "hangman's" knots.

Extracorporeally tied knots are obviously much easier to tie than intracorporeally tied knots, but extracorporeally tied knots can be very difficult to place effectively. A number of devices have been developed to assist in placing an extracorporeally tied knot including the "Clarke" ligator, the "Weston" ligator (see "A New Cinch Knot", Obstetrics & Gynecology, Vol. 78, No. 1, Jul. 1991, 144–47) and other devices. See, e.g., "An Improved Needleholder for Endoscopic Knot Tying", Fertility and Sterility, Vol. 58, No. 3, Sept. 1992, 640–42; "Roeder Knot for Tight Corners in Conventional Abdominal Surgery", J.R. Coll. Surg. Vol. 36, Dec. 1991, 412; "A Simple Method for Ligating with Straight and Curved Needles in Operative Laparoscopy", Obstetrics and Gynecology, Vol. 79, No. 1, Jn. 1992, 143–47. Most of the devices for placing an extracorporeally tied knot fall into the category of "knot pushers". A knot is formed extracorporeally and is pushed through the cannula by sliding it down the material using a device that engages the knot. The Clarke ligator mentioned above was one of the first knot pushers. It simply consists of a grasping end and an end opposite the grasping end with an open ring. It engages the knot by passing the material through the opening in the ring.

There are also a number of patented knot pushers, including those described in U.S. Pat. No. 5,234,445 by Walker, U.S. Pat. No. 5,234,444 by Christondias, U.S. Pat. No. 5,217,471 by Burkhart, U.S. Pat. No. 5,192,287 by Fournier, U.S. Pat. No. 5,163,946 by Li, U.S. Pat. No. 5,129,912 by Noda, U.S. Pat. No. 5,133,723 by Li, U.S. Pat. No. 5,084,058 by Li, U.S. Pat. No. 3,871,379 by Clarke, and U.S. Pat. No. 2,012,776 by Roeder. There are also a number of patents directed more towards endoscopic knotters, including U.S. Pat. No. 5,234,443 by Phan, U.S. Pat. No. 5,211,650 by Noda, U.S. Pat. No. 4,961,741 by Hayhurst, U.S. Pat. No. 4,923,461 by Caspari, U.S. Pat. No. 4,890,614 by Caspari, U.S. Pat. No. 4,641,652 by Hatterer, and U.S. Pat. No. 4,602,635 by Mulhollan. It is believed that an important limitation to these devices is that they do not include a disposable knot carrier in the manner of the present invention.

SUMMARY OF THE INVENTION

The present invention is a method, apparatus, and system for placing a pre-tied extracorporeal knot, with particular but not exclusive application to laparoscopy. The knot may be a slip knot or some other knot, especially a knot that can be formed by passing the free end through a knot body which incudes a loop or set of loops.

A device is disclosed which includes a knot pusher assembly that comprises a knot carrier tube with three concentric ferrules. One of these ferrules is threaded or otherwise removably attached to one of the ends of the knot carrier tube so that the ferrule and the tube share one flush end and the knot carrier tube extends beyond the ferrule and extracorporeally at the other end. A second ferrule is slidably attached concentrically over the first ferrule. A tab on the first ferrule limits the range of motion of the second ferrule. The second ferrule is not as long as the first ferrule so that the first ferrule extends beyond both ends of the second ferrule regardless of the sliding of the second ferrule.

A third ferrule is located concentrically around the first ferrule and is attached to the second ferrule. The third ferrule is radially spaced apart from the first ferrule to define an annular space therebetween. The third ferrule is attached to the second ferrule so that they slide together.

The knot material including a knot or a partially formed knot is wound around the first ferrule in the annular space defined between the first and third ferrules. One end of the knot material is attached to the second ferrule. The other end of the knot material extends off of the flush edge of the first ferrule and the knot carrier tube and terminates at a needle.

A knot release tube is placed concentrically around a segment of the knot carrier tube. One edge of the knot release tube abuts against the edge of the second ferrule opposite the edge of the second ferrule that connects to the third ferrule. The knot release tube extends towards the end of the knot carrier tube opposite the end to which the first ferrule attaches, but does not reach that end so that the knot carrier tube protrudes beyond the knot release tube. The purpose of the knot release tube is to allow the second ferrule to be slid over the first ferrule in the direction of the flush end of the first ferrule and the knot carrier tube. This occurs when the end portion of the knot carrier tube without the first ferrule is held fixed and the knot release tube is pushed in the direction of the second ferrule.

The knot and knot material are deployed by the sliding of the second ferrule towards the flush end of the first ferrule and the carrier tube after the needle has been passed around an object to be tied (or some other knot need is met) and then passed into the device in the space bounded by the ferrules. The end ridge of the second ferrule pushes the windings of the knot material off of the first ferrule. The windings are wound around the mating ferrule to form an at least partially formed knot, and when a sufficient number of windings are pushed off of the first ferrule the free ends of the knot material may be tensioned to form a complete knotted loop.

It is an object of the invention to provide a disposable cartridge that contains the knot material and knot so that multiple knots may be quickly, easily, and inexpensively placed. In an embodiment of the present invention, the three ferrules, knot material, and knot may be inexpensively manufactured in bulk. The three ferrules are made of molded plastic. The second ferrule is placed around the first ferrule and the knot material, such as standard suture material, is wound over the first and second ferrules as described above. The third ferrule is then placed over the windings and attached to the second ferrule and the cartridge is complete. After a completed knot has been separated from the ferrules, the spent cartridge may simply be removed from the knot carrier tube and a new cartridge may be reloaded onto the knot pusher to place another knot.

Although the system is described principally in the preferred embodiment of laparoscopy applications, it can be appreciated that the system is also suitable for many other intracorporeal and extracorporeal applications.

DETAILED DESCRIPTION OF THE INVENTION

Figure 1:
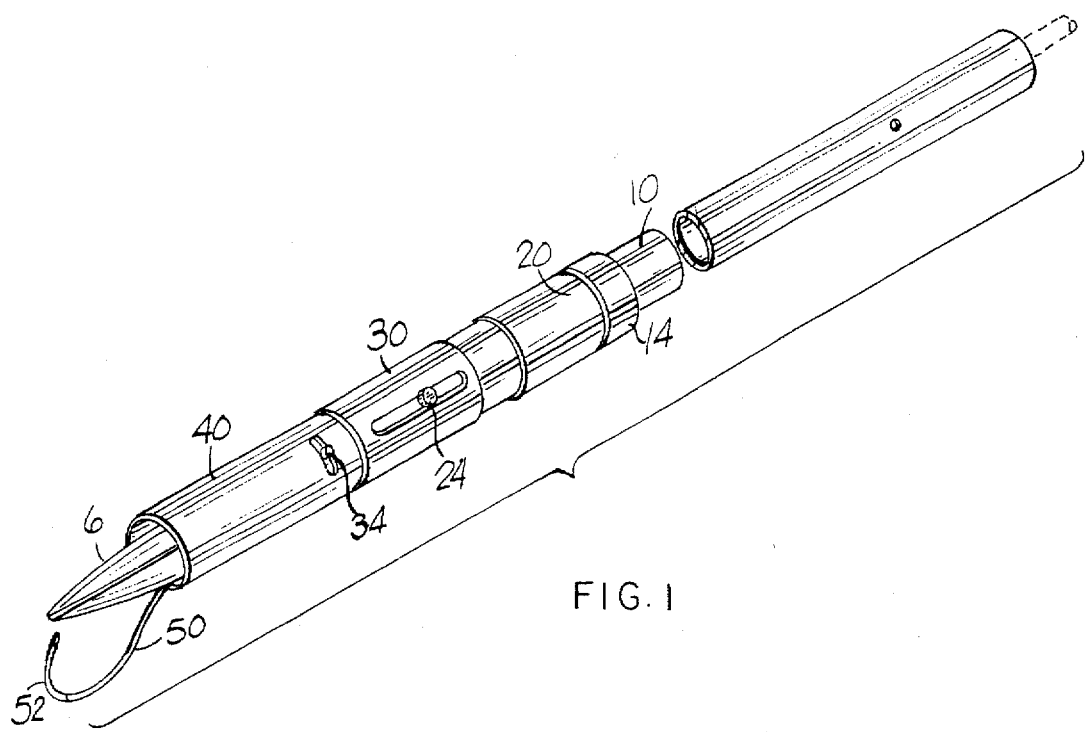
FIG. 1 shows a perspective view of an apparatus in accordance with the present invention.
Figure 3:
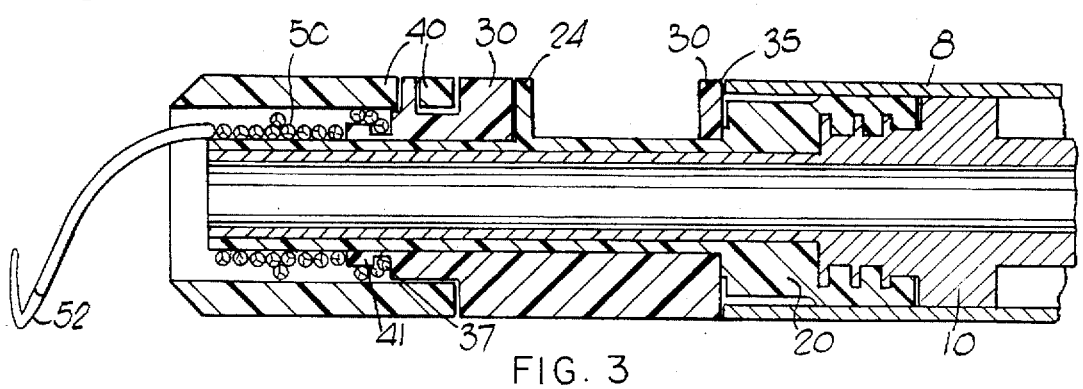
FIG. 3 shows a detailed side-sectional view of the knot deployment end of the apparatus depicted in FIG. 1 before the knot material has been released.
Figure 4:
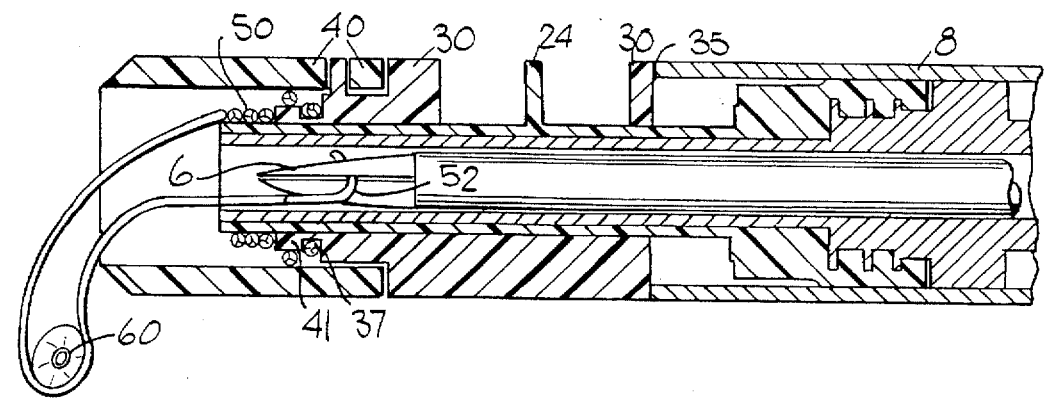
FIG. 4 shows the view of FIG. 3 after the knot material has been partially released.
Figure 2:
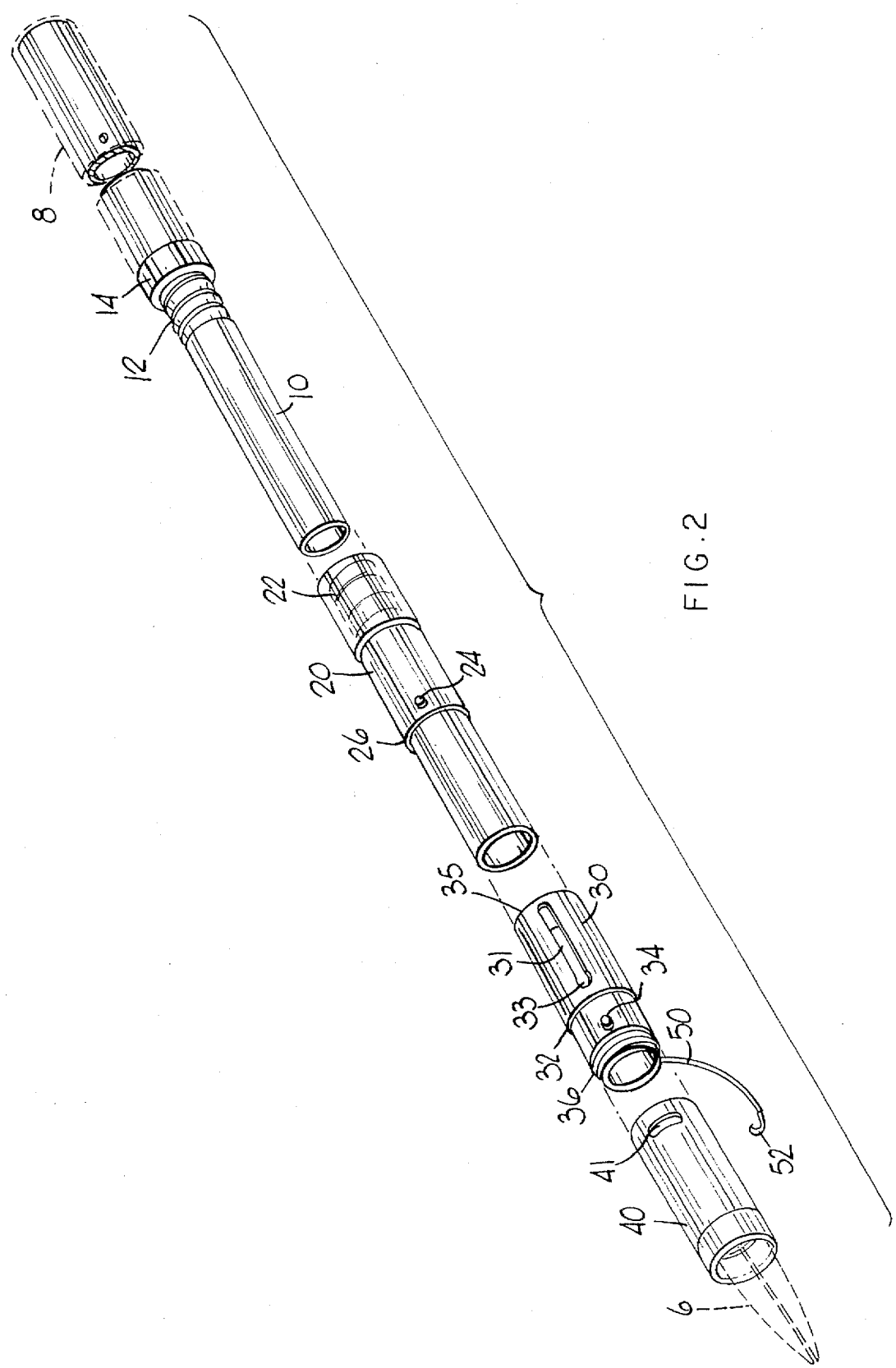
FIG. 2 shows an exploded view of the components of the apparatus of FIG. 1.

A perspective view of a portion of the preferred embodiment of the invention is shown in FIG. 1, including a knot carrier tube 10, a mating ferrule 20, a proximal ferrule 30, a distal ferrule 40, knot material 50, needle 52, and knot material clenching jaws 6. An exploded view of these components is shown in FIG. 2, and detailed side-sectional views are shown in FIGS. 3 and 4. The mating ferrule 20, proximal ferrule 30, and distal ferrule 40 are all co-axial with the knot carrier tube 10. In a preferred embodiment of the invention, the mating ferrule 20 fits around the knot carrier tube 10 so that one end of the mating ferrule 20 is flush with an end of the tube 10 and that threads 22 on the inside of the other end of the mating ferrule 20 mate with threads 12 on the outside of the knot carrier tube 10. The knot carrier tube 10 extends beyond the threaded end of the mating ferrule 20.

In this description of an embodiment of the invention, the direction towards the flush end of the knot carrier tube 10 and the mating ferrule 20 is termed the "distal" direction and the direction towards the opposite end of the knot carrier tube 10 and the mating ferrule 20 is termed the "proximal" direction. The distal direction may extend beyond the flush ends of the knot carrier tube 10 and the mating ferrule 20 and the proximal direction may extend beyond the opposite end of the knot carrier tube 10. "Longitudinal" and "tangential" as used herein are with respect to the axis of the knot carrier tube 10.

An annular ridge 14 is located on the knot carrier tube 10 immediately proximal to the knot carrier tube 10 threads 12 so that the mating ferrule 20 will abut against the ridge 14 when the mating ferrule 20 is completely threaded around the knot carrier tube 10. At that point, no further rotation of the mating ferrule 20 is possible.

The proximal ferrule 30 is slidably located around the mating ferrule 20. A protrusion 24 on the mating ferrule 20 extends through a slot 31 in the proximal ferrule 30 so that the proximal ferrule 30 may be slid longitudinally over the mating ferrule 20 for the the length of the slot 31. When the proximal ferrule 30 is positioned as far to the proximal end as possible (i.e., when the protrusion 24 contacts the distal end of the slot 31), the proximal ferrule 30 abuts against an annular edge 26 of the mating ferrule 20. The slot 31 has an irregularity 33 at its distal end so that the protrusion 24 will achieve an interference fit in the irregularity 33. The initial position of the proximal ferrule 30 is with the protrusion 24 fit into the irregularity 33.

The distal ferrule 40 is located partially around the proximal ferrule 30 and is attached thereto so that sliding the proximal ferrule 30 also slides the distal ferrule 40. The distal ferrule 40 abuts against an annular edge 32 located on the proximal ferrule 30. The annular edge 32 is located distal to the slot 31 on the proximal ferrule 30. The distal end of the distal ferrule 40 extends beyond the distal end of the proximal ferrule 30 and concentrically around the mating ferrule 20 to define an annular space between the mating ferrule 20 and the distal ferrule 40. The distal ferrule 40 is attached to the proximal ferrule 30 by the extension of a protrusion 34 located on the proximal ferrule 30 through a slot 41 located on the distal ferrule 40. The slot 41 is only as wide as the protrusion 34 so that the distal ferrule 40 is fixed with respect to the proximal ferrule 30 in the longitudinal direction.

The knot material 50 is wound around the distal portion of the proximal ferrule 30 with windings extending beyond the distal edge of the proximal ferrule 30 and onto the mating ferrule 20. With reference to FIG. 3, the placement of the windings relative to the mating ferrule 20, proximal ferrule 30, and distal ferrule 40 may be understood. FIG. 3 depicts the knot material 50 when the proximal ferrule 30 is placed in its initial position. The windings of the knot material 50 begin in an annular notch 37 formed in the distal end of the proximal ferrule 30. While two windings are shown in the notch 37 in FIG. 3, the notch 37 may be dimensioned to hold any number of windings. The windings of the knot material 50 pass from the notch 37 over an annular ridge 41 in the proximal ferrule 30 and continue around the mating ferrule 20 in the annular space between the mating ferrule 20 and the distal ferrule 40. The windings pass over the distal edge of the mating ferrule 20 and continue so that a strand of knot material 50 extends beyond the edge the mating ferrule 20 and hangs free from the ferrules and the knot carrier tube 10. This strand of knot material is terminated at a needle 52. The knot material 50 is wound around the mating ferrule 20 so that a desired partially formed knot will result when a sufficient number of windings of the knot material 50 have been pushed off of the mating ferrule 20.

A knot release tube 8 is placed concentrically around a segment of the knot carrier tube 10, as shown in FIGS. 2, 3 and 4. One edge of the knot release tube 8 abuts against the edge 35 of the proximal ferrule 30 opposite the edge of the proximal ferrule 30 that connects to the distal ferrule 40. The knot release tube 8 extends towards the proximal end of the knot carrier tube 10, but does not reach that end so that the knot carrier tube 10 protrudes beyond the knot release tube 8. The purpose of the knot release tube 8 is to allow the proximal ferrule 30 to be slid over the mating ferrule 20 is the distal direction. This occurs when the proximal end of the knot carrier tube 10 is held fixed and the knot release tube 8 is pushed in the distal direction. Thus, the proximal ferrule 30 can be moved by manipulating the proximal ends of the knot release tube 8 and the knot carrier tube 10.

It is a primary object of the present invention to allow a knot to be placed near its desired final position before releasing the knot material 50 from the mating ferrule 20 by positioning the knot carrier tube 10 in close proximity to the desired final position of the knot. Afterwards, the needle 52 is passed around the feature to be tied and then placed into the region partially enclosed by the tube 10 and the ferrules. Next, the knot material 50 is released from the mating ferrule 20, and the free ends of the knot material 50 are tensioned to form a completed knot around a feature.

With reference to FIG. 4, the deployment of the knot material 50 away from the mating ferrule 20 may be understood. By manipulating the knot release tube 8 and the knot carrier tube 10, the proximal ferrule 30 is slid in the distal direction. As discussed above, sliding the proximal ferrule 30 also slides the attached distal ferrule 40. As the ridge 41 on the proximal ferrule 30 moves in the distal direction it forces the knot material 50 towards the distal end of the mating ferrule 20. The windings of the knot material 50 fall off of the edge of the mating ferrule 20 as the ridge 41 moves in the distal direction. As the windings fall off of the edge of the mating ferrule 20 they are no longer bounded by the mating ferrule 20. The knot material 50 is then available distal to the knot carrier tube 10 and may be manipulated by the clenching jaws 6.

The purpose of the annular notch 37 is to anchor an end of the knot material 50. One end of the knot material 50 is tied or otherwise attached to the annular notch 37. If the notch 37 and ridge 41 were not present, tension on the knot material 50 that is exterior to the mating ferrule 20 could pull all of the knot material 50 off of the mating ferrule 20 and the proximal ferrule 30. With the presence of the ridge 41, however, tension on the knot material 50 will pull the strands of the knot material 50 located in the notch 37 into the ridge 41 so that the knot material 50 will remain attached to the proximal ferrule 30.

Note that the ridge 41 does not completely enclose the knot material 50. The ridge 41 does not extend in the radial direction completely to the distal ferrule 40, because knot material 50 must be allowed to pass across the ridge 41. The strand or strands of knot material 50 that wrap around the notch 37 in the proximal ferrule 30 must be sufficiently tensioned so that the strand or strands wrapped around the notch 37 will not pass over the ridge 41. The initial tension on the windings of knot material 50 around the mating ferrule 20 is sufficient to prevent the knot material 50 from sagging away from the mating ferrule 20 but is not so great as to hinder the sliding of the knot material 50 off the mating ferrule 20 when the proximal ferrule 30 is slid. The tension of the winding material 50 may be controlled by, for instance, a cinch knot located in the notch 37 in the proximal ferrule 30.

The distal ferrule 40 serves several functions. It protects the knot material 50 from contamination and from becoming tangled on foreign objects before the knot material 50 is deployed. During the knot deployment process, the distal ferrule 40 aids the sliding of the knot material 50 off of the mating ferrule 20 by limiting the amount of potential overlap of the windings of the knot material 50 and preventing the windings from piling over each other. Because the windings are wound so as to form a particular partial knot, it is important that they are pushed off of the mating ferrule 20 in the correct order.

The annular edge 32 of the proximal ferrule 30 that abuts the distal ferrule 40 facilitates the sliding of the distal ferrule 40. Longitudinal force on the proximal ferrule 30 will be transmitted to the distal ferrule 40 over the entire surface of the annular edge 32 instead of merely at the slot 41 and the slot protrusion 34. Also, the longitudinal force on the proximal ferrule 30 is applied evenly around the circumference of the distal ferrule 40 instead of only at the location of the slot 41.

Figure 5A:
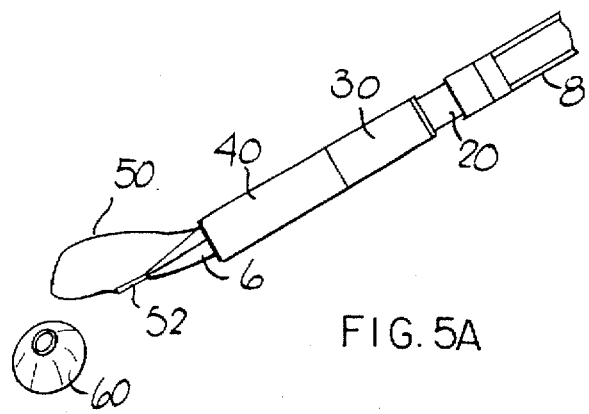
FIGS. 5A, 5B, 5C, and 5D show a perspective view of a released knot being finished.
Figure 5B:
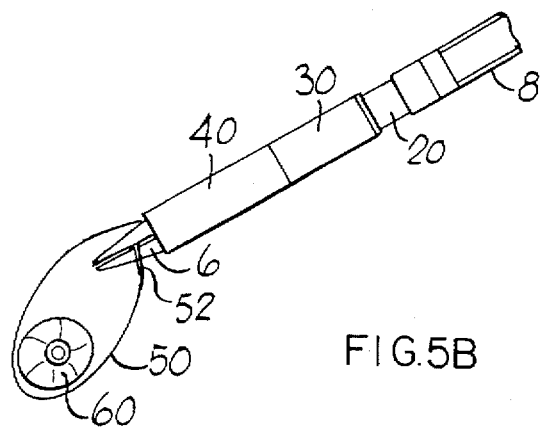
Figure 5C:
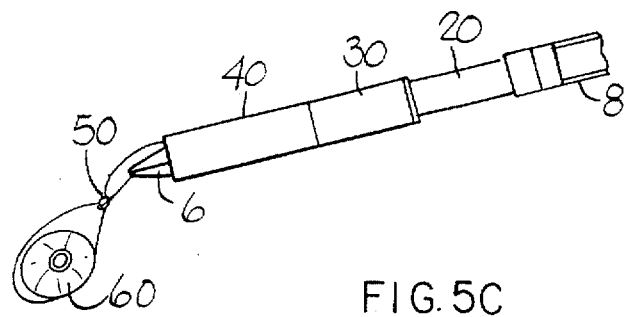

Details of the process of passing the needle 52 through the knot and completing the knot tying process are described in U.S. application Ser. No. 08/182,609 filed on Jan. 17, 1994, of which this application is a continuation-in-part. With reference to FIG. 5A, the needle 52 is placed in the clenching jaws 6 and the knot carrier tube 10 is positioned in the vicinity of the object such as a vessel 60 to be tied. As shown in FIG. 5B, the needle 52 is taken from the clenching jaws 6 and passed through or around vessel 60 and returned to the clenching jaws 6 (such as by use of an additional grasper), and then pulled inside the distal end of the knot carrier tube 10 to allow the windings of knot material 50 in which a partial knot is formed to be draped distal to the needle 52 and over a portion of the knot material 50 attached to the needle 52. As shown in FIG. 5C, the knot material 50 is released from the carrier tube 10 by pushing the release tube 8 while holding the carrier tube 10 fixed, which causes the ridge 41 of the proximal ferrule 30 to slide the knot material 52 off of the mating ferrule 20. The releasing of the knot material 50 allows the knot to lightly cinch down on the lead end of the material which is grasped by the clenching the jaws 6.

Figure 5D:
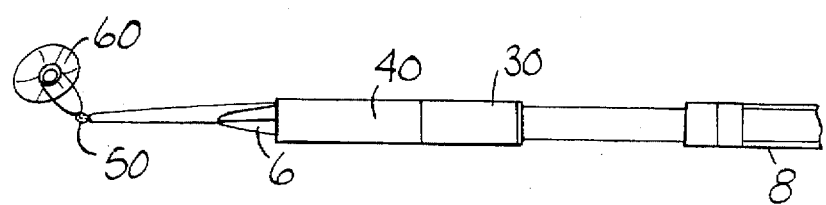

As shown in FIG. 5D, the leads of the knot are tensioned to firmly tie the vessel 60. This may be accomplished by moving the jaws 6 in the proximal direction while keeping the knot carrier tube 10 fixed or by use of a plunger assembly as described in U.S. application Ser. No. 08/182,609. The leads of the knot material 50 may then by cut, either immediately adjacent to the knot or away from the knot to leave longer loose ends as desired.

In a preferred embodiment of the invention, the mating ferrule 20, proximal ferrule 30, distal ferrule 40, and knot material 50 are assembled in bulk and serve as a disposable knot carrying cartridge. The mating ferrule 20, proximal ferrule 30, and distal ferrule 40 are made of molded plastic. The knot carrying material 50 is standard medical suture material. The proximal ferrule 30 is placed over the mating ferrule 20 so that the protrusion 24 of the mating ferrule fits into the irregularity 33 in the slot 31 of the proximal ferrule 30. Any desired knot, such as a square knot or a Roeder knot, is formed in the knot material 50 and a free end of the knot material 50 is terminated with a needle 52. The knot material 50 is wound around the mating ferrule 20 and the proximal ferrule 30, with the needle 52 and an amount of knot material 50 hanging free off of the mating ferrule 20 and the remaining free end of the knot material 50 terminated in the annular notch 37 in the proximal ferrule 30. The termination in the notch 37 may be a cinch knot.

The knot material 50 is wound with sufficient tension so that the windings will remain stationary with respect to each other and the cartridge before the knot deployment process is initiated, but not so tight as to prevent the knot material 50 from sliding along the mating ferrule 20 when the knot deployment process is initiated. The cartridge is completed by placing the distal ferrule 40 over the proximal ferrule 30 so that the protrusion 34 of the proximal ferrule 30 fits through the slot 41 of the distal ferrule 40.

The distal ferrule 40 prevents the knot material 50 from losing too much tension. If the windings start to detach from the mating ferrule 20, they will come into contact with the distal ferrule 40 before they can further unwind.

In a preferred embodiment, the knot carrier tube 10 is manufactured of metal. Unlike the knot carrying cartridge, the knot carrier tube 10 is designed to be used repeatedly. As previously described, the cartridge is installed for use on the knot carrier tube 10 by screwing the mating ferrule 20 onto the appropriate end of the knot carrier tube 10. After the cartridge is used to tie a knot, the cartridge is simply unscrewed and a new cartridge may be installed when needed.

It should be appreciated that other embodiments of the invention may produce substantially the same results by the same methods as has been hereinabove described. As an example, the knot carrier tube and the mating ferrule could be combined as one piece having the same shape as the connected mating ferrule 20 and knot carrier tube 10. This would be particularly useful to produce a completely disposable knot placing device and is an alternate design. As another example, the proximal ferrule 30 and the distal ferrule could be combined as one piece, although this may complicate the manufacturing process.

What is claimed is:

1. A knot placement apparatus, comprising:

a knot carrier spool having a proximal end and a distal end;

a knot slider slidably attached to the knot carrier spook;

thread having a first end and a second end and an at least partially formed knot between the two ends, the thread being initially wound around the knot carrier spool and the at least partially formed knot being initially positioned on the knot carrier spool distal to the knot slider;

whereby sliding the knot slider distally pushes the at least partially formed knot distal to the knot carrier; and wherein the knot slider is a sheath that snugly fits around the knot carrier spool at a position proximal to the at least partially formed knot, and a thread segment containing the second end of the thread is attached to the sheath; and wherein the sheath contains an annular notch and a portion of the thread segment attached to the sheath is wound around the annular notch.

2. A knot placement apparatus, comprising:

a knot carrier spool having a proximal end and a distal end;

a knot slider slidably attached to the knot carrier spool;

thread having a first end and a second end and an at least partially formed knot between the two ends, the thread being initially wound around the knot carrier spool and the at least partially formed knot being initially positioned on the knot carrier spool distal to the knot slider;

whereby sliding the knot slider distally pushes the at least partially formed knot distal to the knot carrier; and wherein the knot slider is a sheath that snugly fits around the knot carrier spool at a position proximal to the at least partially formed knot, and a thread segment containing the second end of the thread is attached to the sheath; and further comprising a thread cover, the thread cover attached to the sheath proximal to the thread segment containing the second end of the thread, the thread cover extending distally beyond the knot carrier, and the thread cover being spaced away from the spool so that the thread segment containing the at least partially formed knot initially resides between the knot carrier and the thread cover.

3. The apparatus of claim 2, wherein the sheath is permanently attached to the thread cover.

4. A knot placement apparatus, comprising:

a knot carrier spool having a proximal end and a distal end;

a knot slider slidably attached to the knot carrier spool;

thread having a first end and a second end and an at least partially formed knot between the two ends, the thread being initially wound around the knot carrier spool and the at least partially formed knot being initially positioned on the knot carrier spool distal to the knot slider;

whereby sliding the knot slider distally pushes the at least partially formed knot distal to the knot carrier; and wherein the knot slider is a sheath that snugly fits around the knot carrier spool at a position proximal to the at least partially formed knot, and a thread segment containing the second end of the thread is attached to the sheath;

an elongate tube having a distal end and a proximal end, wherein the spool is attached to the distal portion of the tube;

means for sliding the sheath, the means being accessible from the proximal portion of the elongate tube; and wherein the means for sliding the sheath comprise an actuating tube that overlaps the elongate tube, one end of the actuating tube abutting the proximal portion of the sheath, and the other end of the actuating tube being located between the sheath and the proximal end of the elongate tube.

5. The apparatus of claim 9, further comprising a needle, wherein a thread segment containing the first end of the thread extends distal to the knot carrier and attaches to the needle.

6. The apparatus of claim 10, further comprising a clamp slidably housed within the elongate tube that may be slid in the proximal direction from an initial position at approximately the distal end of the elongate tube, and where the clamp may be operated from the proximal portion of the elongate tube.

7. A knot placement apparatus, comprising:

a knot carrier spool having a proximal end and a distal end;

a knot slider slidably attached to the knot carrier spool;

thread having a first end and a second end and an at least partially formed knot between the two ends, the thread being initially wound around the knot carrier spool and the at least partially formed knot being initially positioned on the knot carrier spool distal to the knot slider;

whereby sliding the knot slider distally pushes the at least partially formed knot distal to the knot carrier; and wherein the knot slider is a sheath that snugly fits around the knot carrier spool at a position proximal to the at least partially formed knot, and a thread segment containing the second end of the thread is attached to the sheath; and wherein the sheath has an initial position from which the sheath may slide distally, and means for preventing the sliding of the sheath from its initial position until a threshold force is applied;

wherein the means for preventing the sliding of the sheath from its initial position until a threshold force has been applied comprises: a slot having a distal and a proximal end with an irregularity in its distal end placed in the sheath, and a protrusion from the knot carrier that initially fits into the irregularity of the slot, whereby the protrusion forms an interference fit in the irregularity of the slot.

* * * * *